US010576249B2

(12) United States Patent
Guo

(10) Patent No.: US 10,576,249 B2
(45) Date of Patent: Mar. 3, 2020

(54) MEDICAL DEVICE INCLUDING AN ACTUATOR RESTRAINING ASSEMBLY

(71) Applicant: ST. JUDE MEDICAL, CARDIOLOGY DIVISION, INC., St. Paul, MN (US)

(72) Inventor: Xiaoping Guo, Eden Prairie, MN (US)

(73) Assignee: St. Jude Medical Cardiology Division, Inc., St. Paul, MN (US)

( * ) Notice: Subject to any disclaimer, the term of this patent is extended or adjusted under 35 U.S.C. 154(b) by 277 days.

(21) Appl. No.: 14/861,249

(22) Filed: Sep. 22, 2015

(65) Prior Publication Data

US 2016/0089126 A1 Mar. 31, 2016

Related U.S. Application Data

(60) Provisional application No. 62/057,511, filed on Sep. 30, 2014.

(51) Int. Cl.
*A61M 25/01* (2006.01)
*A61B 17/00* (2006.01)

(52) U.S. Cl.
CPC .............. *A61M 25/0147* (2013.01); *A61B 2017/00367* (2013.01)

(58) Field of Classification Search
CPC .......... A61M 25/0147; A61M 25/0136; A61M 25/0133; A61M 25/105; A61M 25/0138; A61B 2017/00318; A61B 2017/00367; A61B 2017/003
See application file for complete search history.

(56) References Cited

U.S. PATENT DOCUMENTS

| | | | | |
|---|---|---|---|---|
| 5,472,017 A | * | 12/1995 | Kovalcheck | A61B 1/0052 138/103 |
| 5,656,030 A | * | 8/1997 | Hunjan | A61M 25/0136 604/264 |
| 5,666,970 A | * | 9/1997 | Smith | A61M 25/0136 600/585 |
| 6,013,052 A | * | 1/2000 | Durman | A61B 18/1492 604/264 |

(Continued)

FOREIGN PATENT DOCUMENTS

EP 1971787 B1 5/2013

OTHER PUBLICATIONS

"Latest Grades of Delrin Acetal", Oct. 3, 2013, Dupont.*
U.S. Appl. No. 61/884,897, filed Sep. 30, 2013.

*Primary Examiner* — Bhisma Mehta
*Assistant Examiner* — Hong-Van N Trinh
(74) *Attorney, Agent, or Firm* — Armstrong Teasdale LLP

(57) ABSTRACT

The present disclosure provides a medical device comprising a restraining assembly configured to assist in restraining a catheter shaft in a deflected configuration. The resistance assembly may include an inner restraining assembly and an outer restraining assembly configured to engage one another and create normal and frictional resistances therebetween sufficient to prevent unintentional and/or undesired proximal, retracting movement of an actuator, and thus, to prevent changes in a desired deflected configuration of the catheter shaft. In one embodiment, the restraining assembly is configured to allow for temporary, i.e., reversible, restraining of the catheter shaft in the deflected configuration.

9 Claims, 15 Drawing Sheets

(56) References Cited

U.S. PATENT DOCUMENTS

| | | | | |
|---|---|---|---|---|
| 6,066,125 | A * | 5/2000 | Webster, Jr. | A61B 5/015 604/528 |
| 7,722,302 | B2 | 5/2010 | Mynhier et al. | |
| 7,997,840 | B2 | 8/2011 | Mynhier et al. | |
| 2002/0165485 | A1 * | 11/2002 | Simpson | A61M 25/0136 604/95.05 |
| 2006/0100640 | A1 * | 5/2006 | Bolduc | A61B 17/00234 606/108 |
| 2007/0282358 | A1 * | 12/2007 | Remiszewski | A61B 17/00 606/159 |
| 2013/0060237 | A1 * | 3/2013 | Ogle | A61M 25/01 604/528 |
| 2013/0144209 | A1 * | 6/2013 | Ryan | A61M 25/0133 604/95.04 |
| 2013/0158379 | A1 * | 6/2013 | Selkee | A61B 1/0052 600/373 |
| 2013/0204096 | A1 * | 8/2013 | Ku | A61B 1/00066 600/301 |
| 2014/0121595 | A1 * | 5/2014 | Tegg | A61B 1/00133 604/95.04 |

* cited by examiner

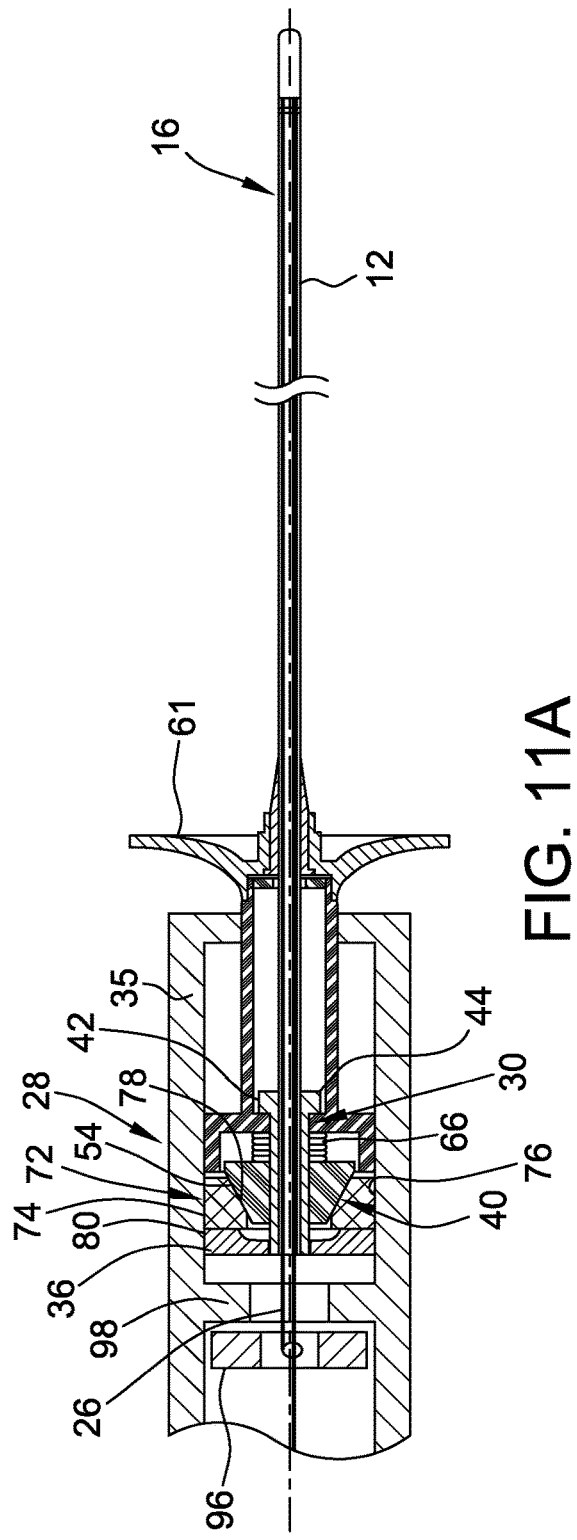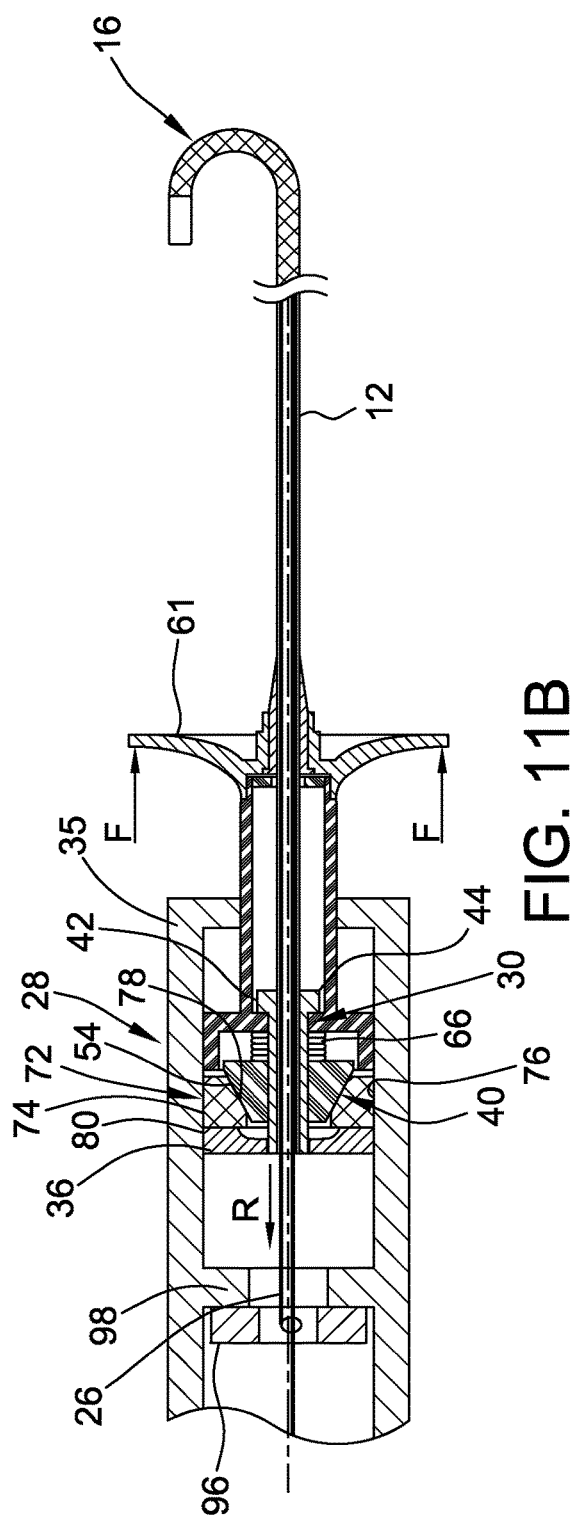
FIG. 11A
FIG. 11B

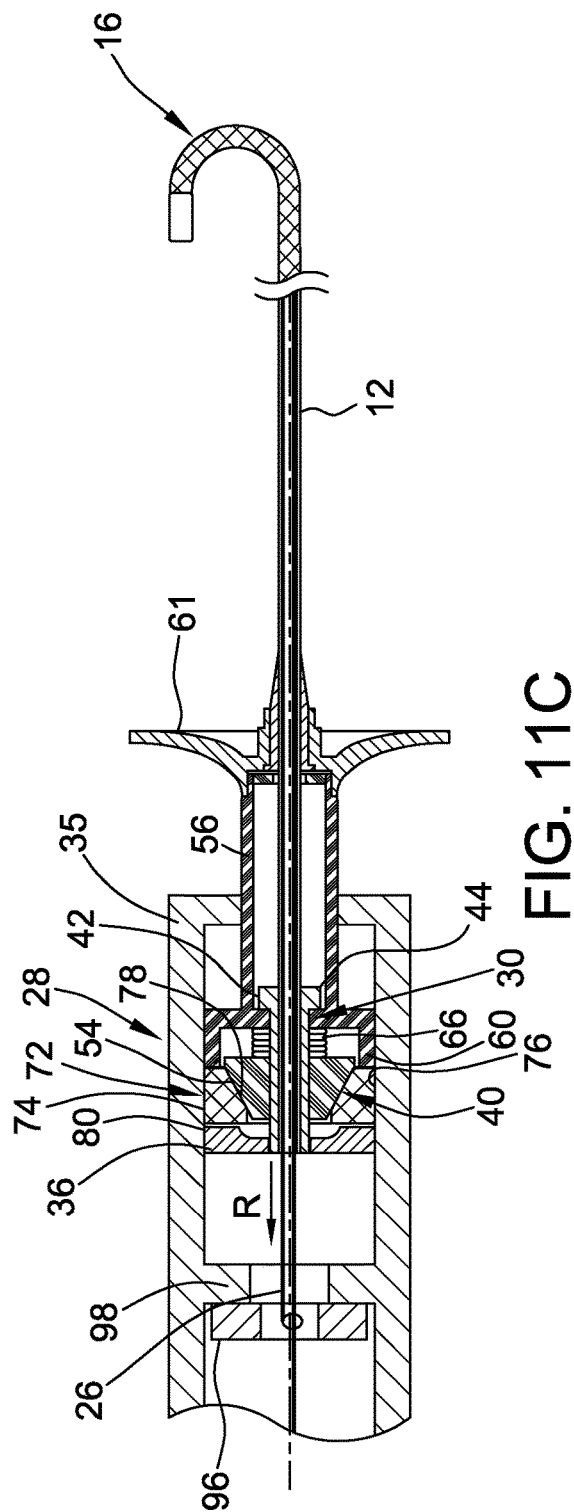
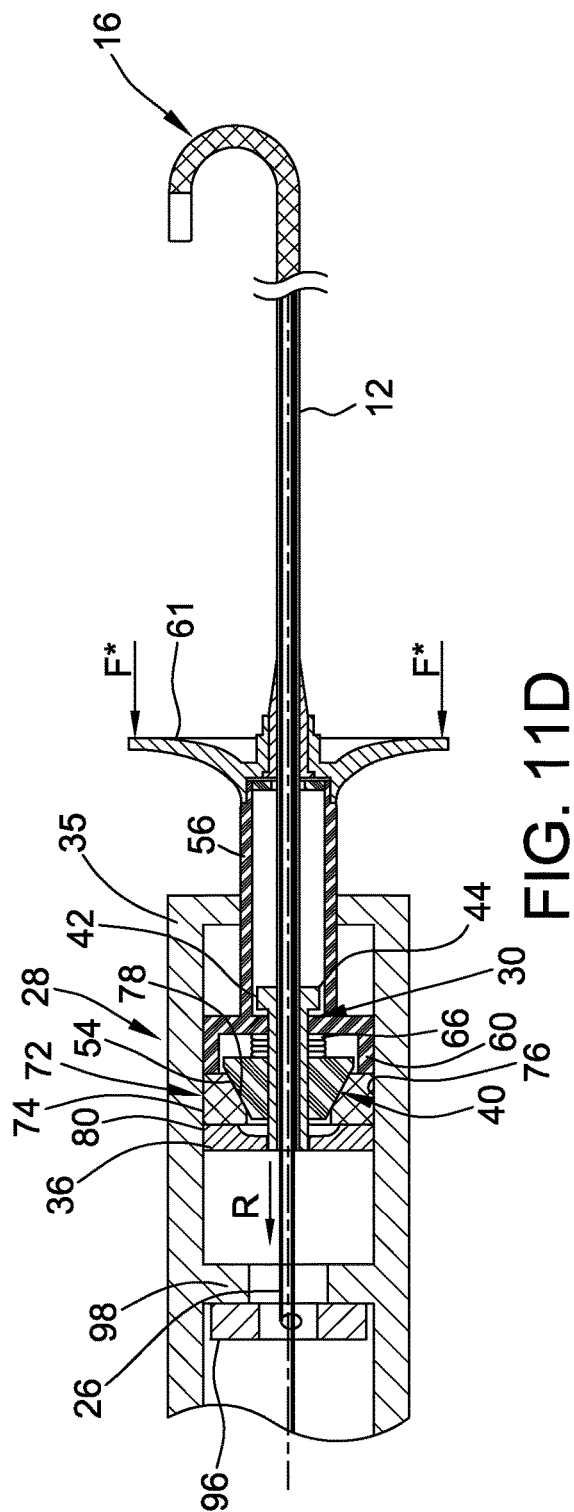
FIG. 11C
FIG. 11D

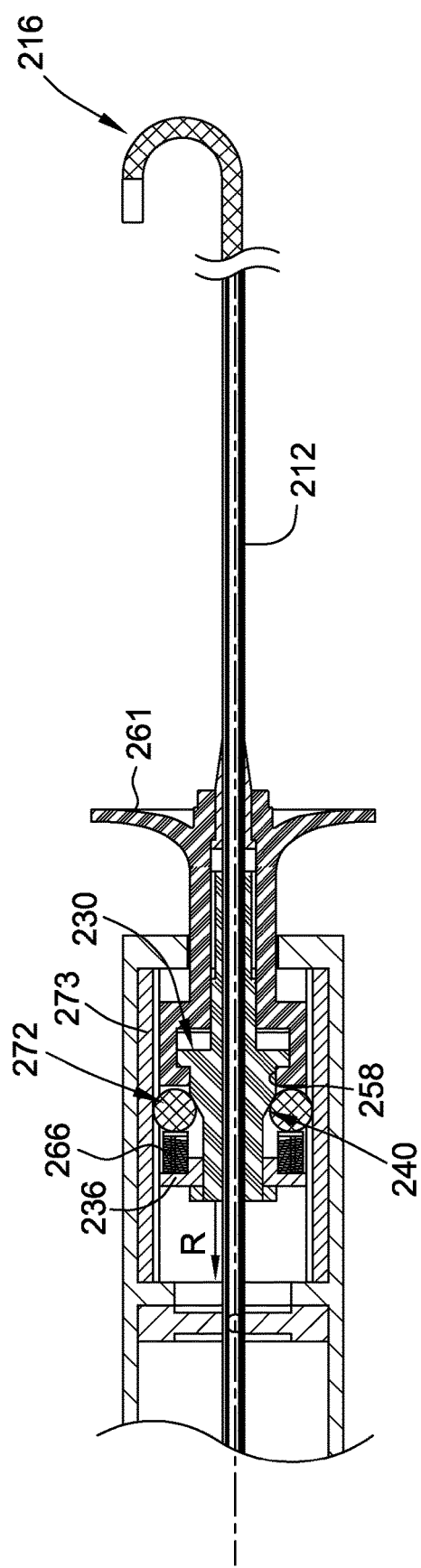
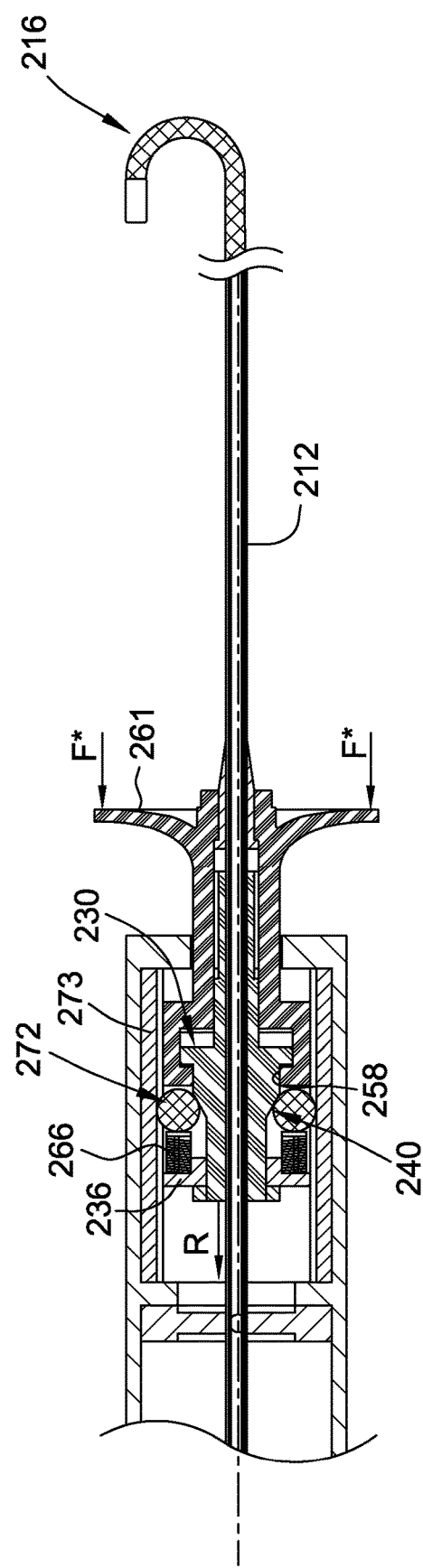

MEDICAL DEVICE INCLUDING AN ACTUATOR RESTRAINING ASSEMBLY

CROSS-REFERENCE TO RELATED APPLICATIONS

This application claims the benefit of U.S. Provisional Patent Application No. 62/057,511, filed Sep. 30, 2014, the entire specification of which is incorporated herein.

FIELD OF THE DISCLOSURE

The present disclosure relates generally to medical devices that are used in the human body. In particular, in many embodiments, the present disclosure relates to a medical device restraining assembly for assisting in holding, retaining, or locking a medical device actuator in a desired position during use, while allowing the release of the medical device actuator to another position as desired.

BACKGROUND

Medical devices, such as catheter systems, are well known in the art for use in medical procedures, such as diagnostic (e.g., cardiac mapping) and therapeutic procedures (e.g., cardiac ablation). Typical catheter systems generally include an elongated flexible catheter shaft extending from a control handle containing an actuating mechanism. A physician manipulates the catheter shaft through the patient's vasculature to an intended site within the patient via the actuating mechanism contained within the control handle.

An actuating mechanism of the catheter system may include mechanical steering features or components that may be manually manipulated to position a catheter shaft within the body at a desired site or to operate the catheter system during use. In some embodiments, a catheter or catheter system may be positioned within a patient's vasculature during a procedure by simultaneous application of torque or force at the proximal end of the catheter and/or by selectively deflecting the distal tip of the catheter in a desired direction.

The distal tip of the catheter can be deflected by a pull wire or other tension member attached or anchored at the distal end of the catheter and extending proximally to an actuator in a control handle that controls the application of tension on the pull wire. Distal movement of the catheter shaft with respect to a body of the control handle, upon the application of an external force on the actuating mechanism, may impose eccentric pull forces on the distal portion of the catheter shaft resulting in the distal portion of the catheter shaft assuming a deflected configuration. Absent an external force exerted on the actuating mechanism, the catheter shaft tends to return to its natural, unstressed position due to the force exerted on it by the strained pull wire.

BRIEF SUMMARY OF THE DISCLOSURE

In one embodiment, the present disclosure is directed to a restraining assembly for a medical device. The restraining assembly comprises an inner restraining assembly positioned within an actuator housing and an outer restraining assembly positioned at least partially between the actuator housing and the inner restraining assembly. At least a portion of a surface of the outer restraining assembly is configured to engage an inner surface of the actuator housing and at least a portion of a surface of the inner restraining assembly thereby providing resistance to movement of the inner restraining assembly in a proximal direction with respect to the actuator housing.

In another embodiment, the present disclosure is directed to a medical device comprising a catheter shaft, an active drive assembly, and a restraining assembly. The catheter shaft has a proximal region and a deflectable distal region, and the active drive assembly comprises a drive lever. The drive lever is configured to engage the proximal region of the catheter shaft and is at least partially movable with respect to an actuator housing along a longitudinal axis thereof. The restraining assembly comprises an inner restraining assembly positioned about the proximal region of the catheter shaft and configured to be axially movable with respect to the actuator housing via the drive lever and an outer restraining assembly positioned at least partially radially between the inner restraining assembly and the actuator housing. The restraining assembly is configured to assist in restraining the deflectable distal region of the catheter shaft in a deflected configuration.

In another embodiment, the present disclosure is directed to a method of deflecting a distal region of a medical device. The method comprises providing a medical device comprising a catheter shaft, an active drive assembly, and a restraining assembly. The catheter shaft has a proximal region and a deflectable distal region, and the active drive assembly comprises a drive lever. The drive lever is configured to engage the proximal region of the catheter shaft and is at least partially movable with respect to an actuator housing along a longitudinal axis thereof. The restraining assembly comprises an inner restraining assembly positioned about the proximal region of the catheter shaft and an outer restraining assembly positioned at least partially radially between the inner restraining assembly and the actuator housing. The method further comprises distally advancing the drive lever with respect to the actuator housing to a position wherein the deflectable distal region of the catheter shaft is in a deflected configuration, and allowing the drive lever to at least partially retract in a proximal direction with respect to the actuator housing such that at least a portion of an outer surface of the inner restraining assembly engages at least a portion of a surface of the outer restraining assembly to create a frictional resistance therebetween sufficient to limit further proximal movement of the drive lever with respect to the actuator housing.

The foregoing and other aspects, features, details, utilities and advantages of the present disclosure will be apparent from reading the following description and claims, and from reviewing the accompanying drawings.

BRIEF DESCRIPTION OF THE DRAWINGS

FIGS. 11A-11D illustrate various intermediate states of the restraining assembly of FIG. 3 in use.

FIGS. 18A-18D illustrate various intermediate states of the restraining assembly of FIG. 13(A-B) in use.

Corresponding reference characters indicate corresponding parts throughout the several views of the drawings. It is understood that that Figures are not necessarily to scale.

DETAILED DESCRIPTION OF THE DISCLOSURE

Figure 1:
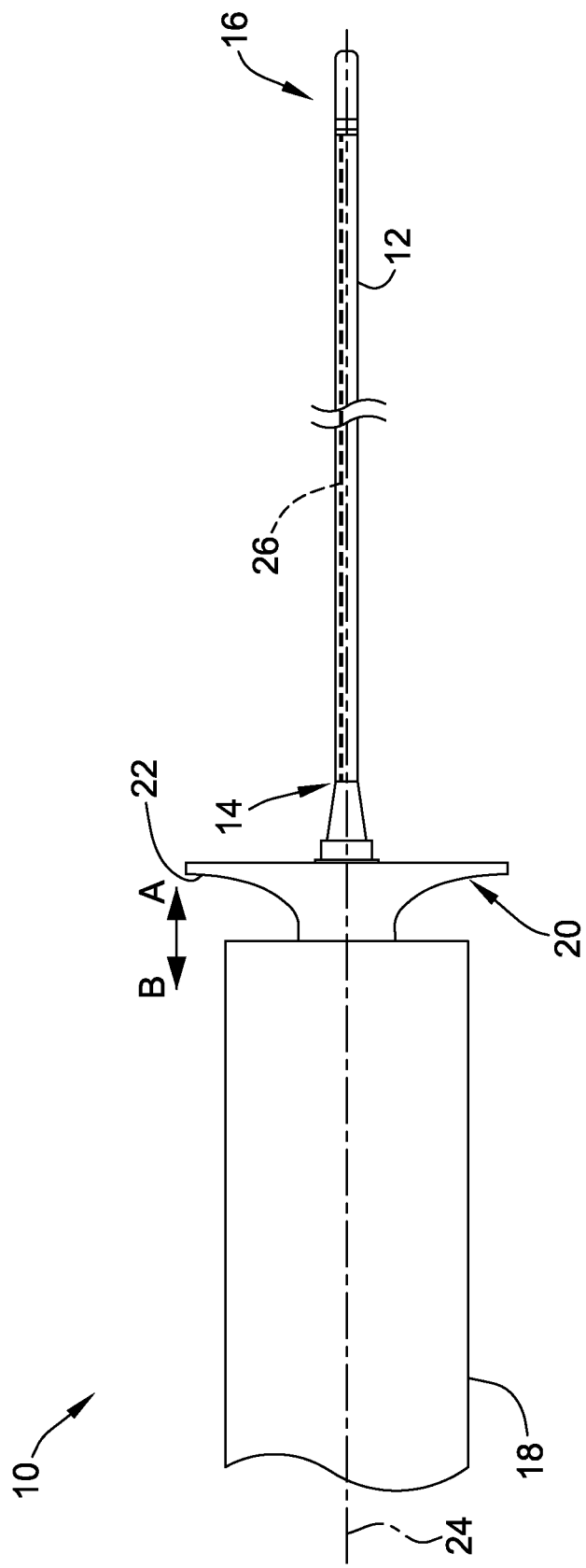
FIG. 1 is a perspective view of one embodiment of a catheter system including a handle, a catheter shaft, and an actuating mechanism.

The present disclosure provides catheter systems suitable for use in the human vasculature for known medical procedures. Catheter systems of the multiple embodiments of the present disclosure exhibit a "self-locking" feature upon the catheter system being positioned in a deflected configuration; that is, the present disclosure provides embodiments wherein an actuator, or actuating mechanism, of a catheter system is restrained in the position in which a distal region of the catheter system is in a deflected configuration, without the need for a user to perform an additional "locking" step to maintain the actuator in the desired position. Because the "automatic" or "self-locking" feature does not permanently fix the actuator in a particular position, the "self-locking" features disclosed herein are also reversible upon the application of a sufficient external force on the actuator in either the proximal direction (to reduce the amount of deflection) or the distal direction (to increase the amount of deflection). Such disclosed embodiments may lead to more consistent and improved patient outcomes. For purposes of this description, the present disclosure will be described in connection with numerous embodiments of a uni-directional plunger-type catheter, including a restraining assembly. It is contemplated, however, that the described features and methods of the present disclosure as described herein may be incorporated into any number of catheters or other medical devices as would be appreciated by one of ordinary skill in the art based on the disclosure herein.

More specifically, some embodiments of the present disclosure provide a catheter system including a restraining assembly comprising an inner restraining assembly positioned at a proximal region of a catheter shaft, and more particularly, about a shaft sleeve that is coupled or affixed to a proximal region of the catheter shaft, and an outer restraining assembly disposed at least partially between an actuator housing and the inner restraining assembly. At least a portion of a surface of the outer restraining assembly is configured to engage an inner wall of the actuator housing while at least another portion of a surface of the outer restraining assembly is configured to engage at least a portion of an outer surface of the inner restraining assembly so as to cause a self-adjusting frictional resistance therebetween sufficient to restrain the actuator in a desired position with respect to the actuator housing. In other words, the outer restraining assembly is configured to be "wedged-in" by the inner restraining assembly under the retraction force arising from the deflection of the catheter shaft. This "wedged-in" configuration causes the outer restraining assembly to be "tightened" against the inner wall of the actuator housing and the actuator to be restrained in a certain position with respect to the actuator housing, while the distal region of the catheter body is in a deflected configuration.

The restraining assembly as described herein provides a mechanistic way by which an actuator may be restrained, or "locked," in a particular position during use of a deflectable catheter system without the need for performing an additional locking step. That is, catheter systems including a deflectable catheter shaft known in the art oftentimes utilize an eccentric pull wire configured to interact with an actuator via a catheter shaft in order to initiate the defection of the distal region of the catheter shaft. As discussed in greater detail below, during use of catheter systems such as these, a user may advance a drive lever (also referred to as an actuator lever) distally, thus causing a proximal end of the pull wire, which may be mounted or fastened to a gripper, to move along with the catheter shaft until such movement is stopped or prohibited by an obstacle (or shoulder) positioned within the handle housing. Continued distal movement of the catheter shaft, driven by the drive lever, creates a high tension on the pull wire. Due to the eccentric fixation of the pull wire to the distal end of the catheter shaft, the tension on the pull wire generates the bending moment imposed on the distal region of the catheter shaft, leading to deflection of the distal region of the catheter shaft. At the same time, the tension on the pull wire leading to the deflection of the distal region results in the actuator or drive lever tending to retract to a neutral (i.e., non-tensioned) state once a distal force is no longer imposed on the actuator. The various embodiments of the restraining assembly described herein provide a frictional resistance to limit undesired and/or unintentional retraction of the drive lever (thus leading to the distal region of the catheter shaft reverting to a "neutral" or "un-deflected" configuration) without the need for a user to perform an additional "locking" step. Further, because the various embodiments of the restraining assembly disclosed herein do not permanently "fix" the actuator (and more particularly the drive lever) in the position corresponding to the deflected configuration of the catheter shaft, a user is able to proximally adjust the actuator during or after a procedure to provide the distal region of the catheter shaft with less or no deflection as compared to the original deflected configuration upon the application of an additional force; that is, the restraining of the actuator in the catheter deflected position is reversible.

Figure 2:
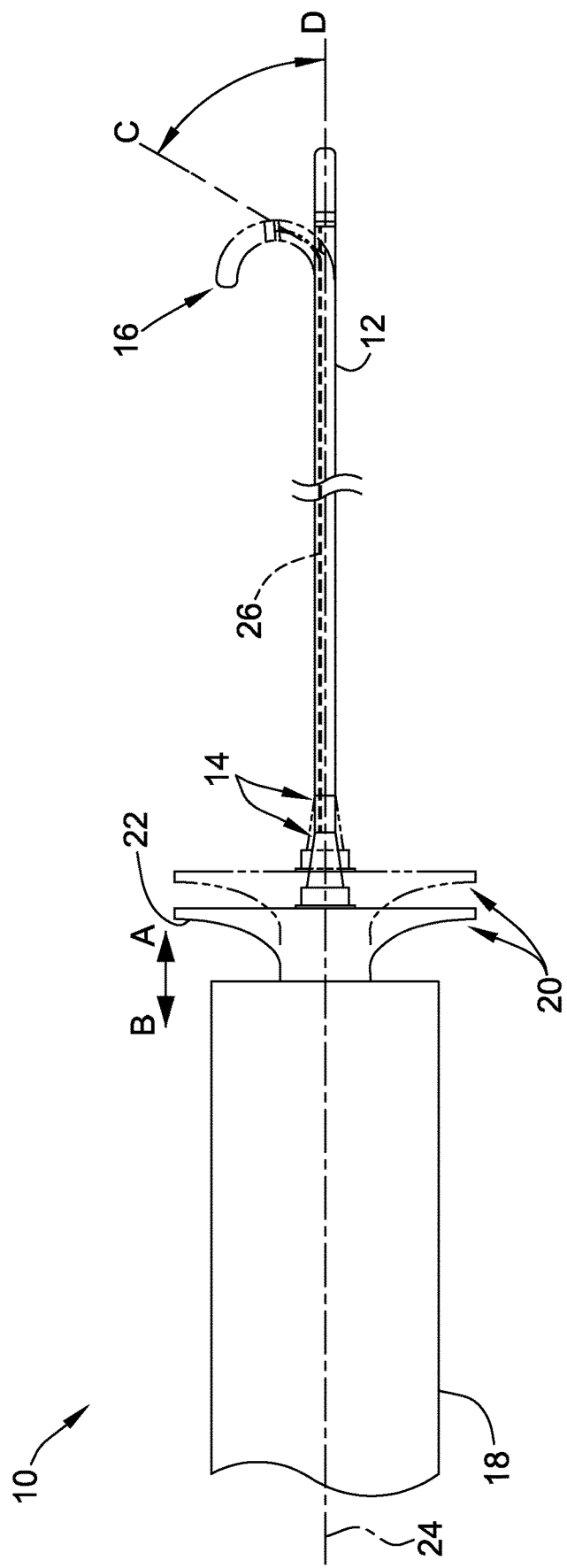
FIG. 2 illustrates the use of a pull wire to deflect the distal end of the catheter shaft of FIG. 1.

Referring now to the drawings, and specifically to FIG. 1, there is shown a plunger-type catheter 10 in an undeflected, or neutral position. Catheter 10 generally includes a catheter shaft 12, having a proximal region 14 and a deflectable distal region 16, a handle 18, and an actuator housing (not shown). Handle 18 includes an actuator mechanism 20. As illustrated in FIGS. 1 and 2 (and as further described below with respect to FIGS. 3 and 5), actuator mechanism 20 includes an drive lever 22 (also referred to as an actuator lever or plunger) that is movable relative to handle 18 along a central, longitudinal axis 24 of handle 18 in a first direction along arrow A (e.g., distally) that effects deflection of distal region 16 of catheter shaft 12 from the neutral position, as well as in a second, opposite direction along arrow B (e.g., proximally) that effects return or retraction of distal region 16 toward the neutral position. For example, catheter 10 can be of the type disclosed in U.S. Provisional Application No. 61/884,897, filed Sep. 30, 2013, which is hereby incorporated by reference as though fully set forth herein.

FIG. 2 illustrates the use of a pull wire 26 for deflecting distal region 16 of catheter shaft 12. Pull wire 26 extends through a lumen of catheter shaft 12. Pull wire 26 is coupled to a pull ring (not shown) embedded in distal region 16 of catheter shaft 12 and to a gripper 27 (shown in FIG. 3), such that movement of drive lever 22 in the first direction along arrow A effects deflection of distal region 16 of catheter shaft 12 from the neutral position along a first deflection direction (e.g., arrow C), and such that movement of drive lever 22 in the second direction along arrow B effects the return or retraction of distal region 16 of catheter shaft 12 towards the neutral position (e.g., along arrow D). Insofar as a person of ordinary skill in the art will appreciate the use of pull wires in a catheter, a detailed explanation of this aspect of the disclosure is not provided herein.

Although the catheter systems disclosed herein are described primarily with respect to unidirectional catheters, it should be recognized that the disclosed principles are equally applicable in other contexts, including but not limited to, bidirectional catheters. That is, for example, with various structural arrangements of the restraining assembly discussed below, movement of drive lever 22 in the first direction along arrow A could affect deflection of distal region 16 from the neutral position in a first defection direction (e.g., arrow C in FIG. 2), while movement of drive lever 22 in the second direction could affect deflection of distal region 16 from the neutral position in a second deflection direction, with both the first and second deflection directions lying in the same plane.

Catheter 10 of FIGS. 1 and 2 may further include a restraining assembly (not shown) configured to restrain catheter shaft 12 in a position corresponding to a deflected configuration of distal region 16 without the need for an additional "locking" step being performed by a user (i.e., the restraining assembly is "self-locking"). That is, the restraining assembly is configured such that upon a user distally advancing drive lever 22 into a first position along arrow A and thus deflecting distal region 16, the restraining assembly remains in the first position, thus holding distal region 16 in the desired deflected configuration upon a user no longer applying any force on drive lever 22. The restraining assembly is also configured to be releasable upon the application of a distal force (i.e., direction A in FIG. 2) or a proximal force (i.e., direction B in FIG. 2) on drive lever 22. As is described in more detail below, the restraining assembly exerts a frictional force arising between components thereof and an actuator housing. That is, the restraining assembly may provide a normal force and a frictional resistance against its impending movement with respect to an actuator housing in a proximal direction (i.e., along arrow B) until a sufficient driving force is applied to drive lever 22 to overcome the frictional resistance exerted by the restraining assembly.

Figure 3:
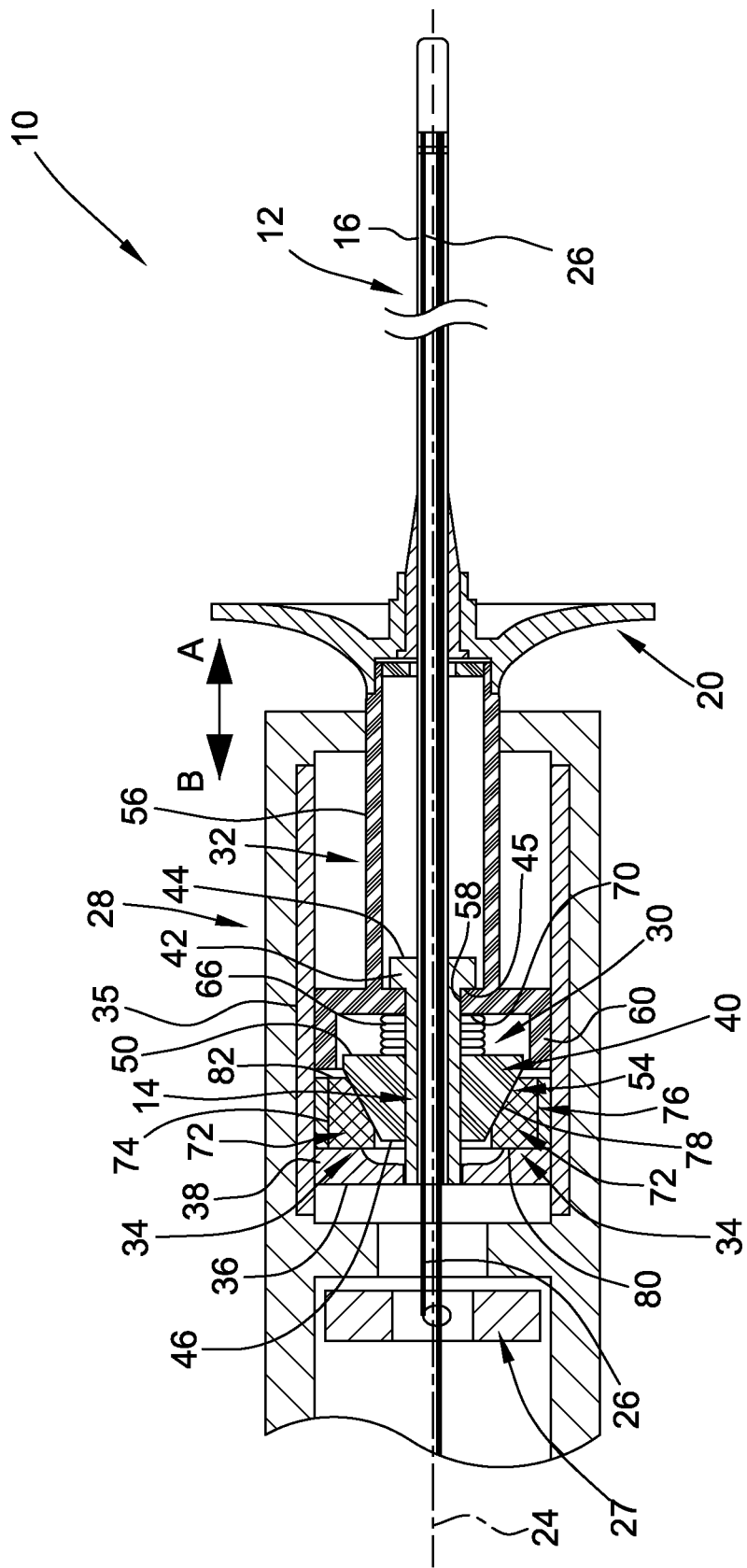
FIG. 3 is a cross-sectional view of the catheter system of FIG. 1 illustrating a cross-section of one embodiment of a restraining assembly.
Figure 4:
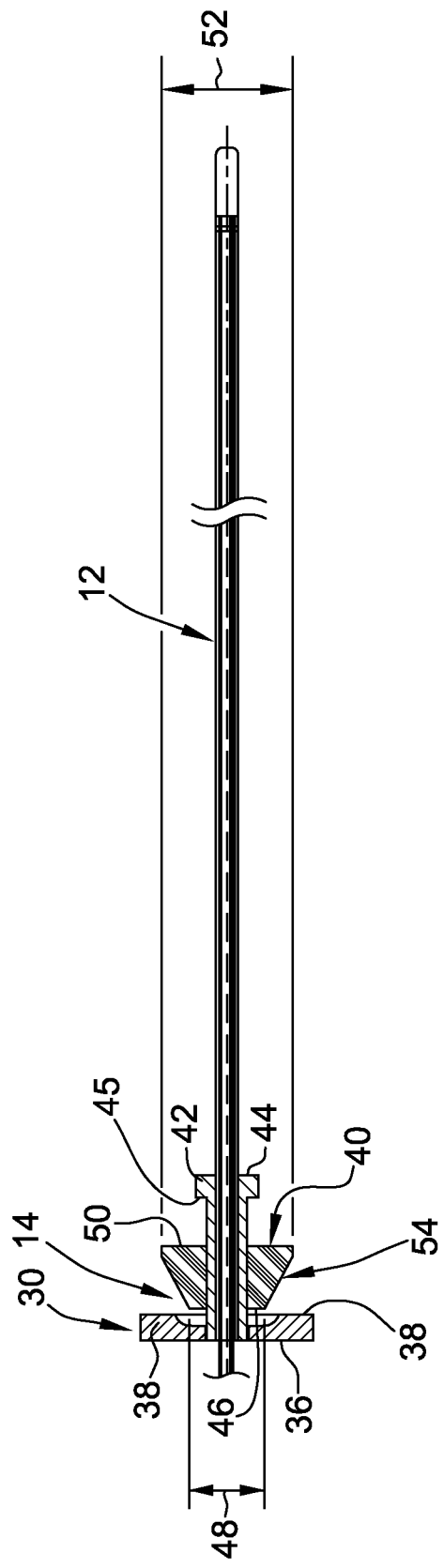
FIG. 4 is a cross-sectional view of an exemplary shaft shuttle assembly of the restraining assembly of FIG. 3.

FIG. 3 illustrates a cross-section of an exemplary restraining assembly for use in catheter 10. Restraining assembly 28 includes a shaft shuttle assembly 30 (shown in FIG. 4), an active drive assembly 32 (shown in FIG. 5), and a friction block assembly 34 (shown in FIG. 6), each positioned within actuator housing 35 as shown in FIG. 3. As shown in FIG. 4, shaft shuttle assembly 30 includes a flat plate 36 with a flange 38 disposed on a distal surface thereof, an inner restraining assembly 40, and a shaft sleeve 42. Flat plate 36 may be permanently or releasably coupled to shaft sleeve 42 such that shaft sleeve 42 extends through flat plate 36. For example, in one embodiment of the present disclosure, flat plate 36 may be slid or threaded onto shaft sleeve 42, positioned in a desired axial position with respect to an inner restraining assembly (discussed in detail below), and permanently affixed to shaft sleeve 42 via a lock screw (not shown) or a suitable adhesive or other chemical agent.

Shaft sleeve 42 includes a rim 44 at a distal end of shaft sleeve 42 creating a shoulder 45 configured to interact with active drive assembly 32, as discussed in more detail below. Shaft sleeve 42 may be permanently or releasably coupled to proximal region 14 of catheter shaft 12 such that catheter shaft 12 extends within and through shaft sleeve 42, as shown in FIG. 4. For example, shaft sleeve 42 may be coupled to catheter shaft 12 via a suitable adhesive or other chemical agent, threads, or any other suitable means. In one particular embodiment of the present disclosure, shaft sleeve 42 is permanently affixed to catheter shaft 12 via any suitable adhesive or chemical agent known in the art capable of providing a suitable bond therebetween.

Inner restraining assembly 40 is permanently (or proximally releasably) coupled to shaft sleeve 42 such that shaft sleeve 42 extends through inner restraining assembly 40. For example, inner restraining assembly 40 may be coupled to shaft sleeve 42 via a suitable adhesive or other chemical agent, threads, or any other suitable means. In one embodiment of the present disclosure, inner restraining assembly 40 may be structurally integrated with shaft sleeve 42 as a single component. In another particular embodiment of the present disclosure, inner restraining assembly 40 is permanently affixed to shaft sleeve 42 via any suitable adhesive or chemical agent known in the art capable of providing a suitable bond therebetween. After assembly and during use, relative axial positions of flat plate 36 and inner restraining assembly 40 with respect to shaft sleeve 42 remain relatively unchanged.

Inner restraining assembly 40 has a proximal end surface 46 having a first diameter 48 and a distal end surface 50 having a second diameter 52 larger than the first diameter 48. In one particular embodiment of the present disclosure, as illustrated in FIGS. 3 and 4, inner restraining assembly 40 is frustoconical in shape including a relatively flat or smooth conic outer surface 54 extending between proximal end surface 46 and distal end surface 50. One skilled in the art will appreciate, however, that inner restraining assembly 40 may have any size or configuration such that it is configured to provide the characteristics thereof set forth in the present disclosure.

Figure 9:
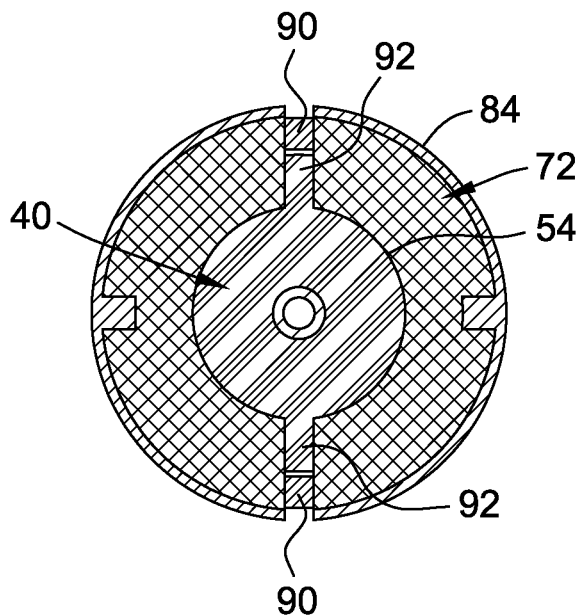
FIG. 9 is a cross-sectional view of an alternative exemplary outer restraining assembly housing for use in the restraining assembly of FIG. 3.

Inner restraining assembly 40 may be formed from any suitable materials such that inner restraining assembly 40 is configured to provide the characteristics thereof set forth in the present disclosure. In some embodiments of the present disclosure, inner restraining assembly 40 is formed of relatively hard and lubricious polymeric materials, such as, but not limited to, acetal homopolymers and copolymers, polycarbonates, polyketones, polyesters, reinforced polyolefins, fluoropolymers, lubricated nylons, or combinations thereof. In one embodiment of the present disclosure, inner restraining assembly 40 may also optionally include one, two, or more division ribs extending from proximal end surface 46 to distal end surface 50 along outer surface 54 (as illustrated in FIG. 9 and discussed in more detail below).

Figure 5:
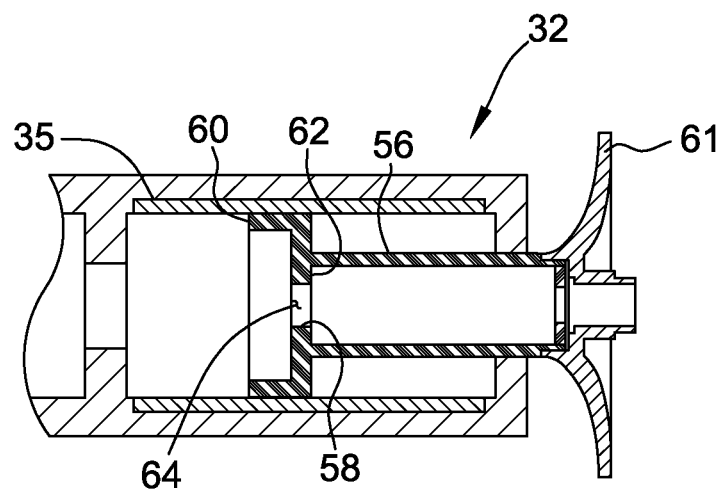
FIG. 5 is a cross-sectional view of an exemplary active drive assembly of the restraining assembly of FIG. 3.

As shown in FIG. 5, active drive assembly 32 includes a drive lever 61 (similar to drive lever 22 discussed with reference to FIGS. 1 and 2 above) and a drive sleeve 56 having an inner rim 58 disposed within and at a proximal end thereof and configured to engage shaft sleeve 42. Drive sleeve 56 also includes a flange 60 disposed at a proximal end thereof and configured to engage friction block assembly 34 during the proximal "unlocking" process of restraining assembly 28, as discussed in detail below.

As discussed in more detail below with respect to the operation of restraining assembly 28, a distal surface 62 of inner rim 58 is configured to engage shoulder 45 of shaft shuttle assembly 30. Further, an opening 64 is disposed at a proximal end of active drive assembly 32 and is sized and configured such that at least shaft sleeve 42 extends therethrough. After assembly of restraining assembly 28, shoulder 45 of shaft shuttle assembly 30 is disposed proximate and engaged with distal surface 62 of inner rim 58 of drive sleeve 56 (as shown in FIG. 3).

At least one compression spring 66 (shown in FIG. 3) may optionally be positioned between distal end surface 50 of inner restraining assembly 40 and a proximal surface 70 of inner rim 58 of drive sleeve 56. When restraining assembly 28 is in a configuration such that it is restraining or holding distal region 16 of catheter shaft 12 in a deflected configuration, as is discussed in more detail below, compression spring 66 may provide protection against external disturbances causing unintentional and/or undesirable movement of friction block assembly 34 and thus "unlocking" of restraining assembly 28. A compression element or spring (shown as 100 in FIG. 12) may also optionally be positioned between flat plate 36 and outer restriction assembly 72 to enhance constant surface contacts or engagements between outer restraining assembly 72 and inner restraining assembly 40 and actuator housing 35.

Figure 6:
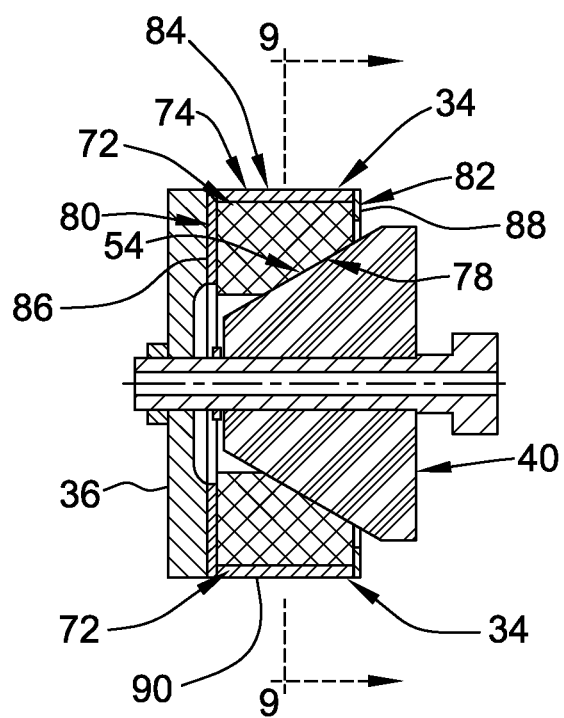
FIG. 6 is a cross-sectional view of an exemplary outer restraining assembly of the restraining assembly of FIG. 3.

FIGS. 6-10 illustrate various embodiments and views of exemplary friction block assemblies 34 and components thereof of the present disclosure. FIG. 6 is a cross-sectional view of an exemplary friction block assembly 34 and its disposition with respect to various components of shaft shuttle assembly 30 of the present disclosure. Friction block assembly 34 includes an outer restraining assembly 72 configured to engage an inner surface of actuator housing 35 and an outer surface of inner restraining assembly 40 and to cause a frictional resistance therebetween sufficient to restrain or hold restraining assembly 28 in a desired position (i.e., a position corresponding to a deflected configuration of the distal region of the catheter body) with respect to actuator housing 35.

In one particular embodiment of the present disclosure, outer restraining assembly 72 has an outer surface 74 configured to engage an inner surface 76 of actuator housing 35 (as shown in FIG. 3), and an inner surface 78 configured to engage outer surface 54 of inner restraining assembly 40. Further, outer restraining assembly 72 has a proximal end surface 80 configured to engage flat plate 36 of shaft shuttle assembly 30, and a distal end surface 82 configured to be able to engage flange 60 of drive sleeve 56 when retracting or "unlocking" restraining assembly 28 (as shown in FIG. 3). One skilled in the art will appreciate that outer restraining assembly 72 may have any size or configuration such that it is configured to provide the characteristics thereof set forth in the present disclosure (see, for example, alternative embodiment outer restraining assembly 272 discussed below).

Outer restraining assembly 72 may be formed from any suitable polymeric materials such that outer restraining assembly 72 is configured to provide the characteristics thereof set forth in the present disclosure. In some embodiments of the present disclosure, outer restraining assembly 72 may be formed of a single material. Suitable materials for forming outer restraining assembly 72, when using a single material, include for example, but are not limited to acrylonitrile butadiene styrene (ABS), polycarbonate, thermoplastic elastomers (e.g., thermoplastic polyurethanes, poly (ether block amide) copolymers, and the like), synthetic rubbers, silicone elastomers, thermoplastic vulcanizates, and the like.

In other embodiments of the present disclosure, outer restraining assembly 72 may be formed of two or more materials. For example, outer restraining assembly 72 may be comprised of a first material for use in forming at least outer surface 74 (and configured to engage inner surface 76 of actuator housing 35) and a second material for use in forming at least inner surface 78 (and configured to engage outer surface 54 of inner restraining assembly 40). In one exemplary embodiment of the present disclosure wherein two materials are used for forming outer restraining assembly 72, the first material (which is configured to engage inner surface 76 of actuator housing 35) may have a higher coefficient of friction than the second material (which is configured to engage outer surface 54 of inner restraining assembly 40). In this embodiment, the first material may be selected from, but not limited to, elastomeric materials such as rubbers and thermoplastic elastomers such as silicone rubbers, natural rubbers, polyamide-based, polyester-based, or polyurethane-based thermoplastic elastomers at durometer values lower than Shore 60D and combinations thereof, such that a suitable coefficient of friction is present between outer surface 74 and inner surface 76. Inner surface 76 of actuator housing 35 may be formed of polymers such as acrylonitrile-butadiene-styrene copolymers, polycarbonate, polyetherimide, polysulfones, and combinations thereof. Further, the second material may be selected from, but not limited to, relatively rigid and lubricious polymers such as acetal homopolymers and copolymers, nylons, fluoropolymers, polysulfones, polyketones, aromatic polyamides, and combinations thereof. In this particular embodiment, the first and second material may be permanently incorporated into one entity via multiple mechanical interlocking sites, thermal bonding, adhesive, or any other suitable means.

In other exemplary embodiments of the present disclosure, the coefficient of friction of inner surface 76 (of outer restraining assembly 72) with outer surface 54 (of inner restraining assembly 40) can be reduced by mechanical means such as, but not limited to, decreases in contact areas therebetween and lubrication of one or both of inner surface 76 or outer surface 54. Mechanical means may also be used in increasing the coefficient of friction between outer surface 74 of outer restraining assembly 72 and inner surface 76 of actuator housing 35, such as, but not limited to, surface modifications including roughening, frictional coatings, and the like.

In one embodiment of the present disclosure, outer restraining assembly 72 is formed of a single unitary member. In this particular embodiment, it may be desirable to use a highly elastomeric material in forming outer restraining assembly 72. In other embodiments, outer restraining assembly 72 comprises two or more members contained within an outer restraining assembly housing 84 configured to contain and circumferentially separate the members disposed therein. Outer restraining assembly housing 84 may be formed from similar materials as inner restraining assembly 40.

Figure 7:
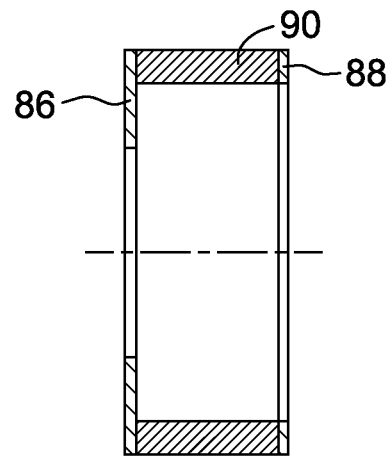
FIG. 7 is a side-view of an exemplary outer restraining assembly housing for use in the restraining assembly of FIG. 3.
Figure 8:
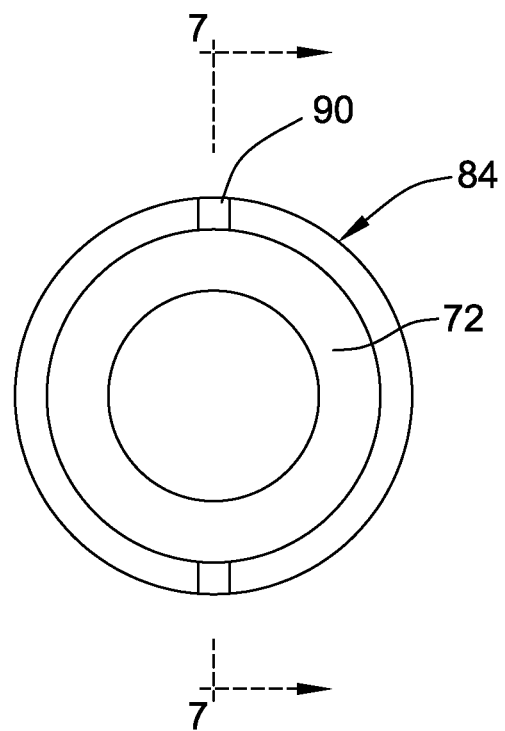
FIG. 8 is a cross-sectional view of the outer restraining assembly housing of FIG. 7.

As shown in FIGS. 6 and 7, housing 84 may include a proximal end plate 86 and a distal end plate 88 with a ligament 90 extending therebetween. (See also FIG. 8 illustrating a cross-sectional view of the housing of FIGS. 6 and 7, and in particular, illustrating a cross-sectional view of ligament 90 extending between proximal end plate 86 and distal end plate 88). Ligament 90 is configured to separate individual members of outer restraining assembly 72. Ligament(s) 90 and end plates 86 and 88 of housing 84 also hold the individual members as one entity so as to aid in their synchronous axial movements relative to inner restraining assembly 40.

Figure 10:
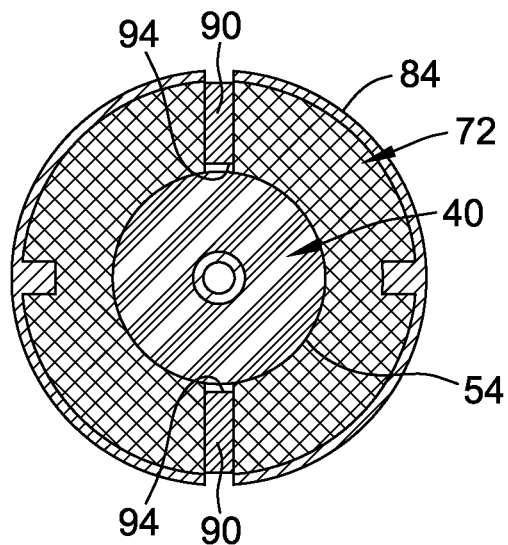
FIG. 10 is a cross-sectional view of an alternative exemplary outer restraining assembly housing for use in the restraining assembly of FIG. 3.

As shown in FIG. 9, in one embodiment of the present disclosure, ligament(s) 90 may be configured to radially align with rib(s) 92, which are optionally positioned along outer surface 54 of inner restraining assembly 40. As shown in FIG. 10, in another embodiment of the present disclosure wherein inner restraining assembly 40 does not include rib(s) 92, ligament 90 is configured to extend such that an inner surface 94 of ligament 90 is substantially parallel to outer surface 54 of inner restraining assembly 40. In this particular embodiment, ligament(s) 90 act as the sole dividers for the two or more members comprising outer restraining assembly 72 within housing 84. Whether or not inner restraining assembly 40 includes ribs 92, outer restraining assembly 72, when configured to be positioned within housing 84, is configured such that when inner restraining assembly 40 tends to move axially, individual members of outer restraining assembly 72 tend to move only in the radial direction with respect to housing 84.

Referring back to FIG. 3, during assembly of restraining assembly 28 at its neutral (i.e., "unlocked" or "un-deflected") configuration, outer restraining assembly 72 is positioned between the spaces formed by flat plate 36, inner restraining assembly 40, and inner surface 76 of actuator housing 35, thus leading to direct surface contacts with flange 38 (of flat plate 36), outer surface 54 (of inner restraining assembly 40), and inner surface 76 (of actuator housing 35). By adjusting the axial position of flat plate 36 along shaft sleeve 42, the "tightness" of the above-referenced surface contacts will vary and may affect the deflection and retraction forces of the deflection of catheter shaft 12. In one embodiment of the present disclosure, at the neutral state of restraining assembly 28, the contact forces at all contact surfaces may be minimal as long as all three surface contacts can be reliably maintained. Hence, components of restraining assembly 28 including flat plate 36, inner restraining assembly 40, and outer restraining assembly 72 would not need to bear high stresses or strains at the neutral state. This may aid in avoiding a stress relaxation phenomena or Payne effects of polymeric materials used to form each of the above-referenced components.

FIGS. 11A-11D illustrate various states of the restraining assembly of FIG. 3 in use. As noted above (and referring to FIG. 6), in the neutral state, as shown in FIG. 11A, the components of restraining assembly 28 are free of loads or are in minimal pre-loads as long as the surface contacts between each of the flat plate 36/distal end surface 82 (of outer restraining assembly 72), outer surface 54 (of inner restraining assembly 40)/inner surface 78 (of outer restraining assembly 72), and inner surface 76 (of actuator housing 35)/outer surface 74 (of outer restraining assembly 72) are substantially maintained.

As illustrated in FIG. 11B, to deflect distal region 16 of catheter shaft 12 to a desired configuration, a driving force F is imposed on drive lever 61, and thus is transferred to shaft shuttle assembly 30 via rim 44 of shaft sleeve 42, which results in the distal movement of inner restraining assembly 40. As drive lever 61 advances distally, distal movement of a pull wire gripper 96 (to which a proximal end of pull wire 26 is coupled) is inhibited due to contact with a ridge 98 positioned at a proximal end of actuator housing 35, which then imposes a pull wire force R on a distal end of pull wire 26 positioned within distal region 16 leading to a deflected configuration. During the distal movement of drive lever 61, inner restraining assembly 40 is moved out of a "locked" state; that is, inner restraining assembly 40 tends to separate, or be "wedged-out" from outer restraining assembly 72 to form an "unlocked" state, thus allowing each of inner restraining assembly 40 and outer restraining assembly 72 (proximally engaged by flat plate 36 of shaft shuttle assembly 30) to move together in a distal direction.

Once a targeted deflected configuration is obtained, driving force F on drive lever 61 is released. Pull wire force R imposed on distal region 16 of catheter shaft 12 tends to retract catheter shaft 12 coupled to shaft shuttle assembly 30 back to its neutral state (i.e., the configuration or state illustrated in FIG. 11A). The impending retraction is along the direction of pull wire force R (i.e., the proximate or retraction direction, e.g., along arrow B of FIG. 3) as illustrated in FIG. 11B. Pull wire force R tends to cause shaft shuttle assembly 30 and active drive assembly 32 retract proximally together (i.e., in the impending retracting direction). The impending retraction introduces an increased normal force on inner surface 78 of outer restraining assembly 72 imposed by outer surface 54 of "wedging-in" inner restraining assembly 40. This normal force further translates to an increased normal force between inner surface 76 (or actuator housing 35) and outer surface 74 (of outer restraining assembly 72), leading to increased friction forces on these contact surfaces. When suitable design and material conditions are met (as is discussed in detail above), a "self-locked" state of restraining assembly 28, and in particular distal region 16 of catheter shaft 12, in a deflected configuration will be automatically introduced by pull wire force R, regardless of the magnitude of pull wire force R. The "self-locked" or "locked" state of restraining assembly 28 is illustrated in FIG. 11C. The impending retraction of shaft shuttle assembly 30 positions, tends to move, or "wedges-in," inner restraining assembly 40 proximally into the space present in the center of outer restraining assembly 72. The resulting relative position of each of inner restraining assembly 40 and outer restraining assembly 72 tends to radially tighten outer restraining assembly 72 against the inner surface 76 of actuator housing 35, thus providing the increased normal forces that generate the static friction forces sufficient to limit the impending retraction of inner restraining assembly 40 and outer restraining assembly 72 with respect to actuator housing 35 together.

To intentionally retract from one deflected configuration to a less deflected configuration or to the neutral state, an additional actuation force F* is imposed on drive lever 61, as illustrated in FIG. 11D. Actuation force F* is transferred to drive sleeve 56 to first compress compression spring 66 (if present) until flange 60 is in contact with distal end surface 82 of outer restraining assembly 72 (or with distal end plate 88 of housing 84 if housing 84 is used in the particular embodiment). Actuation force F*, which may be counteracted by the compressive force of compression spring 66 (if present) but aided by pull wire force R arising from the deflected configuration of distal region 16 of catheter shaft 12, causes outer restraining assembly 72 to be returned to an "unlocked" state; that is, actuation force F* applied (directly or indirectly) to outer restraining assembly 72 causes a separation to occur between inner surface 78 of outer restraining assembly 72 and outer surface 54 of inner restraining assembly 40 and also between outer surface 74 of outer restraining assembly 72 and inner surface 76 of actuator housing 35. This pending separation of surface contacts allows shaft shuttle assembly 30 to move in a proximal direction resulting in distal region 16 of catheter shaft 12 returning to a less deflected (or neutral) configuration.

Once outer restraining assembly 72 is released by actuation force F* (i.e., contacted by flange 60), outer restraining assembly 72 is in contact with flat plate 36 (either directly or via housing 84, if present). As long as actuation force F* is equal to or greater than the overall resistance of restraining assembly 28, the retraction of shaft shuttle assembly 30 may be assisted by pull wire force R. If, during retracting, actuation force F* is reduced, the retracting may discontinue and restraining assembly 28 may move to a "self-locking" position under pull wire force R at a different catheter shaft 12 configuration with less extent of deflection. One skilled in the art will appreciate that to move from a first deflected configuration to a second deflected configuration, wherein the second configuration is more deflected than the first configuration, no "unlocking" of restraining assembly 28 is necessary. That is, to move to the second deflected configuration, driving force F is again imposed distally on drive lever 61 resulting in additional deflection of distal region 16 of catheter shaft 12. When a targeted configuration is obtained, driving force F is released and restraining assembly 28 once again assumes a "self-locking" state.

Figure 12:
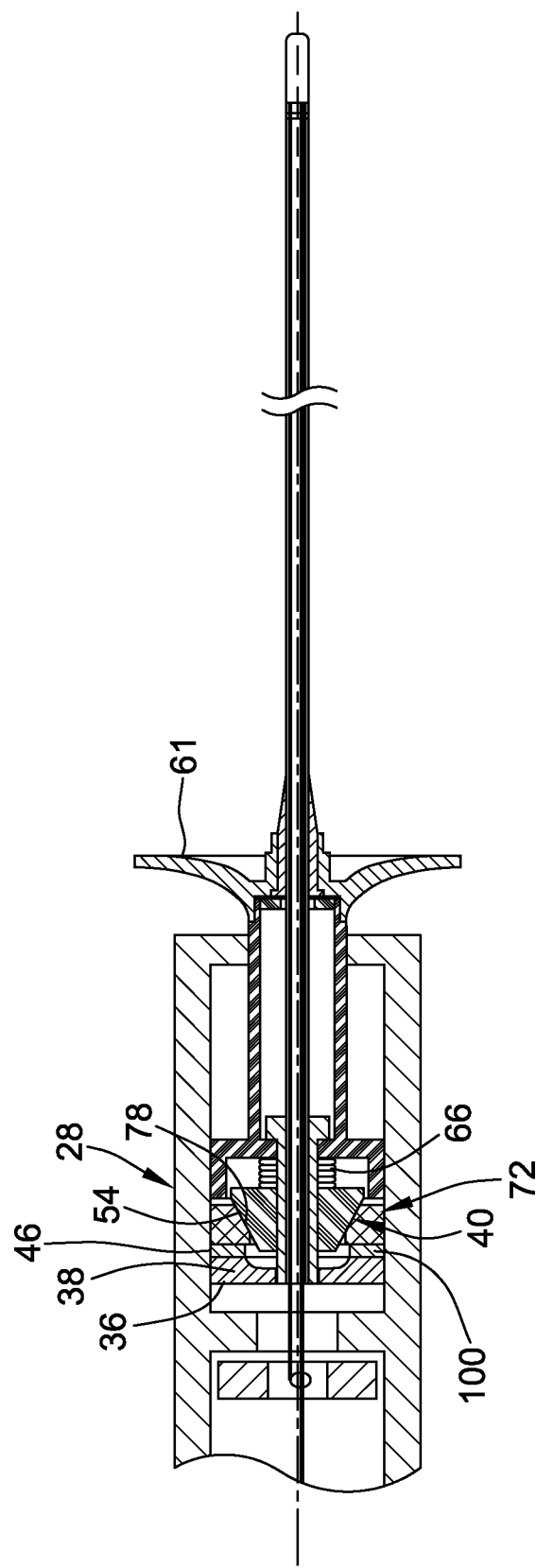
FIG. 12 is a cross-sectional view of the catheter system of FIG. 1 illustrating an exemplary embodiment of a restraining assembly including a compression spring between the active drive assembly and the shaft shuttle assembly.

As noted above, compression spring 66 is an optional component of restraining assembly 28. When present, however, compression spring 66 provides at least some protection against external disturbances or forces acting on drive lever 61 causing restraining assembly 28 to unintentionally and/or undesirably move into an "unlocked" position. In addition to optionally including compression spring 66 to potentially increase the efficiency of restraining assembly 28, restraining assembly 28 may also optionally include a compression element 100 positioned between flange 38 of flat plate 36 and proximal end surface 46 of inner restraining assembly 40 (as shown in FIG. 12). In use, compression element 100 may improve the constant reliability of surface contacts between inner surface 78 (of outer restraining assembly 72) and outer surface 54 (of inner restraining assembly 40) and between outer surface 74 (of outer restraining assembly 72) and inner surface 76 (of actuator housing 35), thus improving the "locking" capability of restraining assembly 28. Compression element 100 may be highly resilient and preferably comprises a metallic spring.

Figure 13:
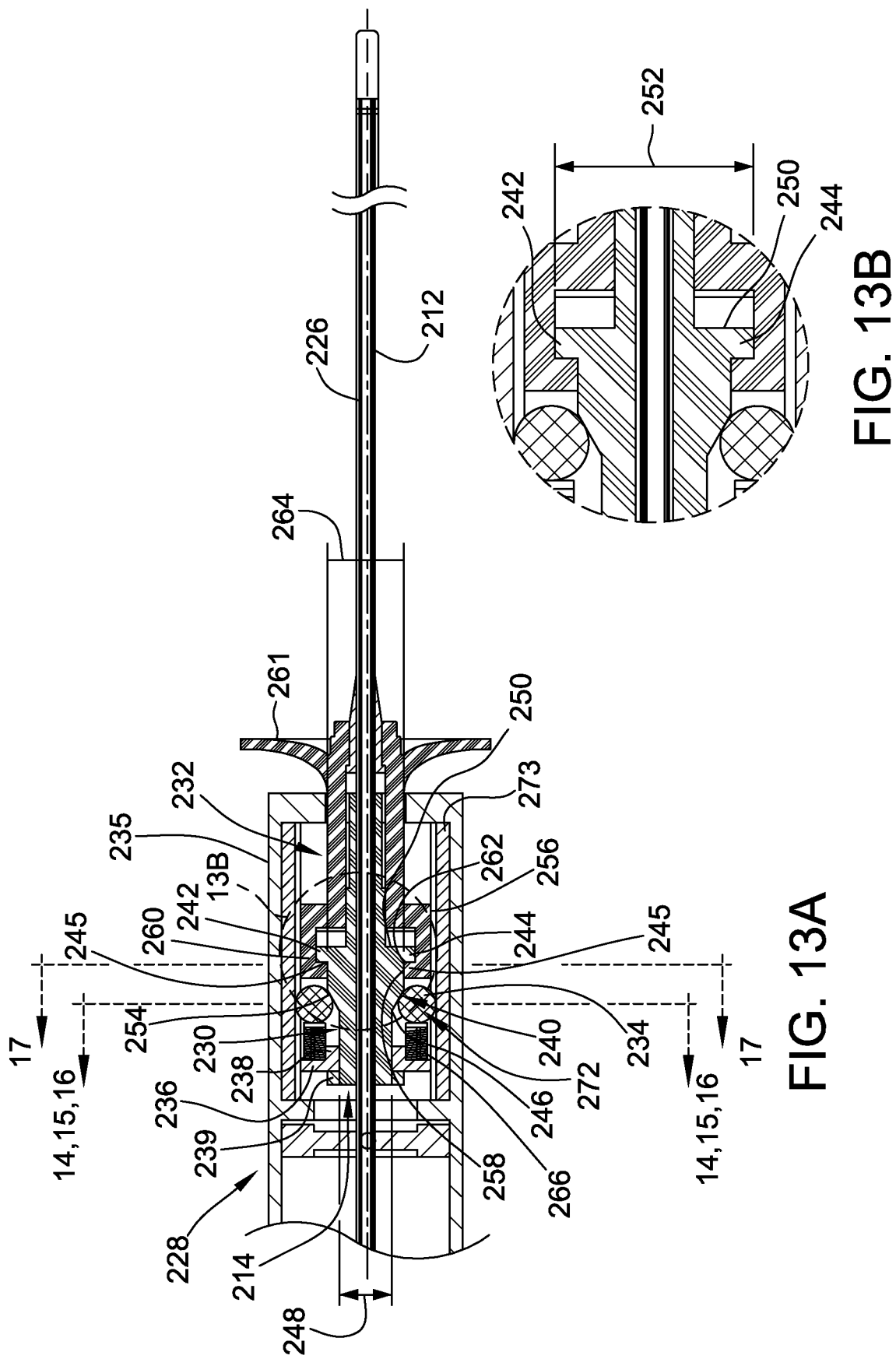
FIG. 13A is a cross-sectional view of the catheter system of FIG. 1 illustrating a cross-section of alternative exemplary embodiment of a restraining assembly.
FIG. 13B is a coss-sectional detailed view of FIG. 13A.

FIG. 13(A-B) illustrates an alternative exemplary embodiment of the present disclosure including a restraining assembly 228. Restraining assembly 228 is similar to restraining assembly 28 shown in FIG. 3 but differs in the size, structural arrangement, and configuration of shaft shuttle assembly 230 (including inner restraining assembly 240), active drive assembly 232, and outer restraining assembly 272. As illustrated in FIG. 13(A-B), and similar to shaft shuttle assembly 30 of FIG. 3, shaft shuttle assembly 230 includes a flat plate 236 with a flange 238 disposed on a distal surface thereof, a shaft sleeve 242 having an inner restraining assembly 240 disposed thereon and a center lumen through which catheter shaft 212 is introduced and coupled thereto. Flat plate 236 may be permanently or releasably coupled to shaft sleeve 242 such that shaft sleeve 242 extends through flat plate 236. For example, in one embodiment of the present disclosure, flat plate 236 may be slid or threaded onto shaft sleeve 242, positioned in a desired axial position with respect to an actuator housing 235 and an outer restraining assembly 272 (discussed in detail below), and permanently affixed to shaft sleeve 242 via a lock screw 239 or a suitable adhesive or chemical agent.

Shaft sleeve 242 includes a rim 244 at a distal end of shaft sleeve 242 creating a shoulder 245 configured to interact with active drive assembly 232, as discussed in more detail below. Shaft sleeve 242 may be permanently or releasably coupled to a proximal region 214 of catheter shaft 212 such that catheter shaft 212 extends within and through shaft sleeve 242. For example, shaft sleeve 242 may be coupled to catheter shaft 212 via a suitable adhesive or other contact agent, threads, or any other suitable means. In one particular embodiment of the present disclosure, shaft sleeve 242 is permanently affixed to catheter shaft 212 via any suitable adhesive or chemical agent known in the art capable of providing a suitable bond therebetween.

In one embodiment of the present disclosure, inner restraining assembly 240 is permanently or releasably coupled to shaft sleeve 242 such that shaft sleeve 242 extends through inner restraining assembly 40. For example, inner restraining assembly 240 may be coupled to shaft sleeve 242 via a suitable adhesive or other chemical agent, threads, or any other suitable means. In one particular embodiment of the present disclosure, catheter shaft 212 is inserted into a center lumen of shaft sleeve 242 and is permanently affixed to shaft sleeve 242 via any suitable adhesive or chemical agent known in the art capable of providing a suitable bond therebetween.

Inner restraining assembly 240 has a proximal end surface 246 having a first diameter 248 and a distal end surface 250 having a second diameter 252 larger than the first diameter. Shaft sleeve 242 may be formed of relatively rigid, lubricious polymeric materials or metallic materials, as discussed above for inner restraining assembly 40 of FIG. 6.

Active drive assembly 232 includes a drive sleeve 256 having a rim 258 disposed at a proximal end thereof. Drive sleeve 256 also includes a flange 260 disposed between drive sleeve 256 and rim 258 and configured to engage friction block assembly 234, and in particular outer restraining assembly 272, during the "unlocking" of restraining assembly 228 as discussed in detail below. Active drive assembly 232 further includes a drive lever 261 (similar to drive lever 22 discussed with reference to FIGS. 1 and 2 above).

As discussed in more detail below with respect to the operation of restraining assembly 228, a distal surface 262 of rim 258 is configured to engage shoulder 245 of shaft shuttle assembly 230. Further, an opening 264 is disposed at a proximal end of active drive assembly 232 and is sized and configured such that shaft sleeve 242 extends therethrough such that at least a portion of inner restraining assembly 240 is disposed on a proximal side thereof and rim 244 is disposed on a distal side thereof.

The space enclosed by an inner surface of drive sleeve 256 and an outer surface of shaft sleeve 242 can be utilized to install a strain relief such as a highly resilient and compliant element, e.g., a flexible spring. In one embodiment of the present disclosure, the axial distance between a distal end of shaft sleeve 242 and the strain relief (not shown) may vary during operation of restraining assembly 228. Similar to compression spring 66 shown in FIG. 3, the strain relief may provide a buffer against disturbance-induced proximal movement of drive lever 261, which tends to trigger the unintentional "unlocking" of restraining assembly 228.

FIGS. 14-17 illustrate various embodiments and views of exemplary friction block assemblies 234 of the present disclosure that may be used in restraining assembly 228, wherein outer restraining assembly 272 has a substantially circular cross-section.

Figure 14:
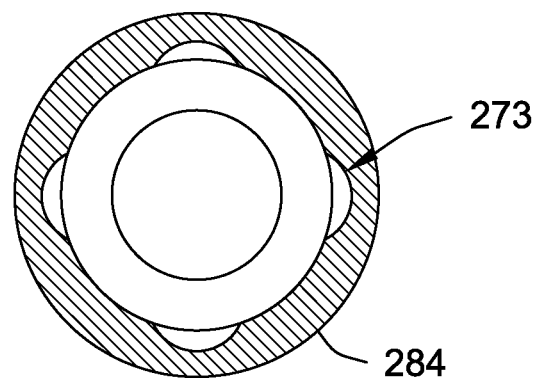
FIGS. 14 and 15 illustrate cross-sectional views of an exemplary embodiment suitable for use in the catheter system of FIG. 13(A-B) wherein the outer restraining assembly includes four spherical members.
Figure 15:
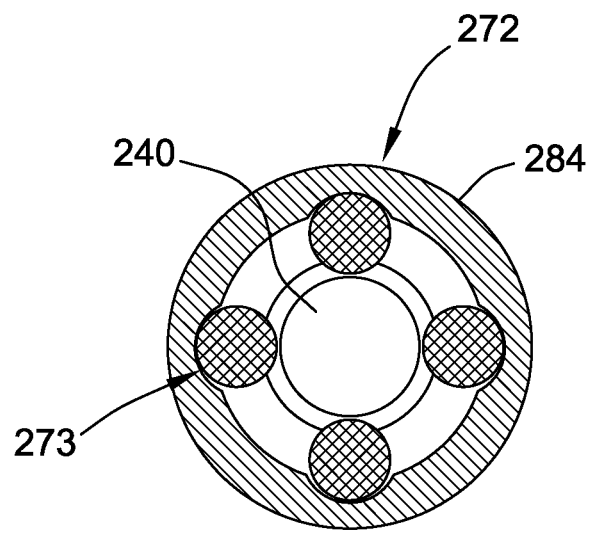

FIGS. 14 and 15 are cross-sectional views of a portion of restraining assembly 228 (as shown in FIG. 13(A-B)) illustrating one embodiment of the present disclosure wherein outer restraining assembly 272 includes four spherical shaped members configured to engage, via point contacts, both inner restraining assembly 240 and an inner surface of roller rails 273 positioned within outer restraining assembly housing 284 (which is disposed concentrically within actuator housing 235). The point contacts may provide seamless and constant surface contacts between outer surface 254 of inner restraining assembly 240 and outer restraining assembly 272, so as to maintain the responsiveness and reversibility of deflection, restraining (i.e., "locking"), "unlocking," and retraction of restraining assembly 228 upon the introduction of a suitable driving force on drive lever 261.

In some embodiments of the present disclosure, outer restraining assembly 272 includes at least two spherical members but may include three, four, five, six, seven, eight or more spherical members. FIGS. 14 and 15 illustrate cross-sections of an exemplary outer restraining assembly 272 for use in restraining assembly 228 of FIG. 13(A-B), wherein outer restraining assembly 272 includes four spherical members. These spherical members are axially movable, but are radially confined by roller (or guiding) rails 273 formed in an inner surface of housing 284. In one embodiment, the contact surface of roller rails 273 with outer restraining assembly 272 has a similar or slightly larger size and configuration of the spherical members of outer restraining assembly 272; that is, roller rails 273 may have the same approximate curvature of a portion of the spherical members such that the spherical members are free to axially move along roller rails 273 but are substantially radially contained within roller rails 273.

Figure 16:
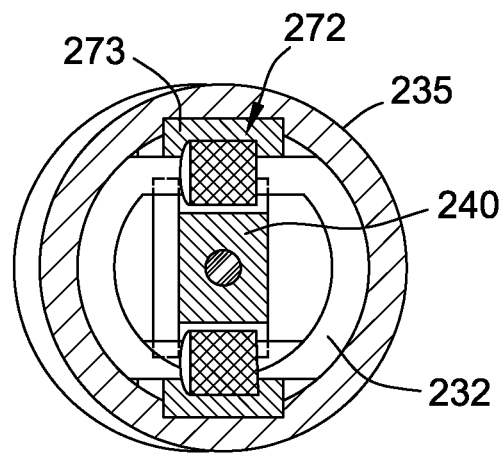
FIG. 16 is a perspective view illustrating a cross-section of an exemplary embodiment suitable for use in the catheter system of FIG. 13(A-B) wherein the outer restraining assembly includes two cylindrical members.
Figure 17:
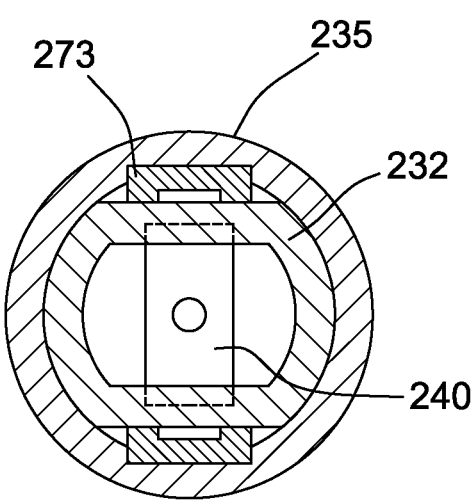
FIG. 17 illustrates a cross-sectional view of the exemplary embodiment of FIG. 16 with the cylindrical members removed.

FIGS. 16 and 17 are cross-sectional views of a portion of restraining assembly 228 (as shown in FIG. 13(A-B)) illustrating another embodiment of the present disclosure wherein outer restraining assembly 272 includes two cylindrical shaped members configured to engage, via line contacts, both a portion of outer surface 254 of inner restraining assembly 240 and an inner surface of roller rails 273. The line contacts may provide seamless and constant surface contacts between outer surface 254 of inner restraining assembly 240 and outer restraining assembly 272, so as to maintain the responsiveness and reversibility of deflection, restraining (i.e., "locking"), "unlocking," and retraction of restraining assembly 228 upon the introduction of a suitable driving force on drive lever 261.

In one embodiment of the present disclosure, outer restraining assembly 272 includes at least two cylindrical members but may include three, four, five, six, seven, eight or more cylindrical members. FIGS. 16 and 17 illustrate cross-sections of an exemplary outer restraining assembly 272 for use in restraining assembly 228 of FIG. 13(A-B), wherein outer restraining assembly 272 includes two cylindrical members. The cylindrical members are axially movable, but are radially confined by roller rails 273 positioned within or affixed to actuator housing 235. In one particular embodiment, roller rails 273 have rectangular grooves configured to receive a cylindrical member of outer restraining assembly 272 therein and are affixed to actuator housing 235. As shown in FIG. 16, which is a perspective view illustrating a cross-section taken along a proximal portion of active drive assembly 232, in this embodiment of the present disclosure, the proximal portion of active drive assembly 232 is relatively flat along a portion parallel to roller rails 273 and is relatively cylindrical along portions extending therebetween, such that active drive assembly 232 generally corresponds in shape to actuator housing 235 with roller rails 273 embedded therein and is movable axially, but is radially constrained.

Referring again to FIG. 13(A-B), restraining assembly 228 may include roller springs 266 to facilitate contacts of outer restraining assembly 272 (and in particular individual members of outer restraining assembly 272) and outer surface 254 of inner restraining assembly 240 and with a portion of roller rail 273 affixed to actuator housing 235. Roller springs 266 are positioned between flat plate 236 (and in particular flange 238) and outer restraining assembly 272. Roller springs 266 may assist in maintaining minimal compression forces against outer restraining assembly 272 such that outer restraining assembly 272 is in contact with portions of outer surface 254 of inner restraining assembly and the inner, or guiding, surfaces of roller rails 273.

Figure 18A:
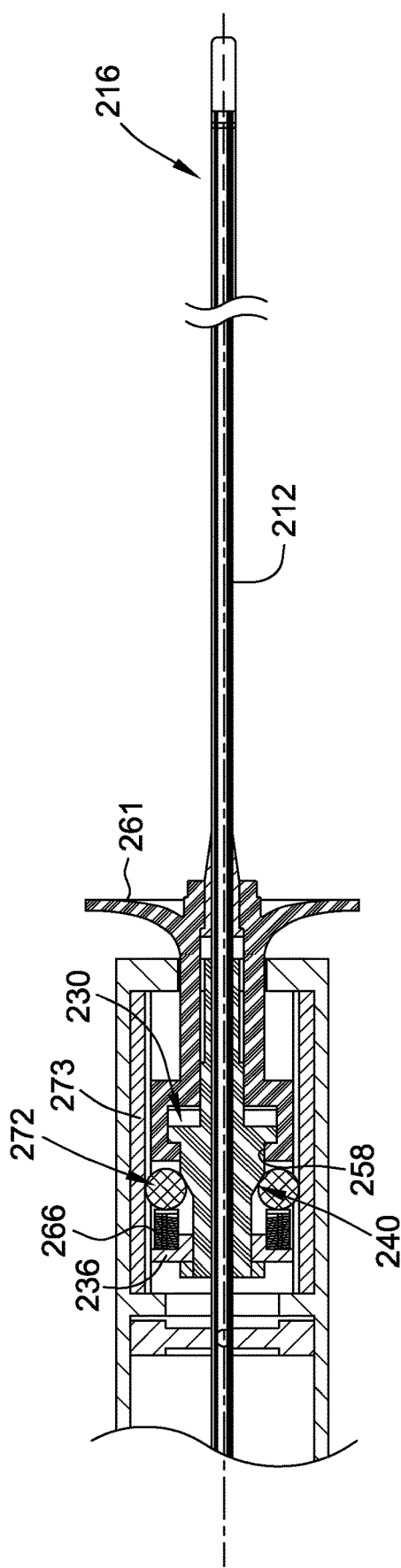
Figure 18B:
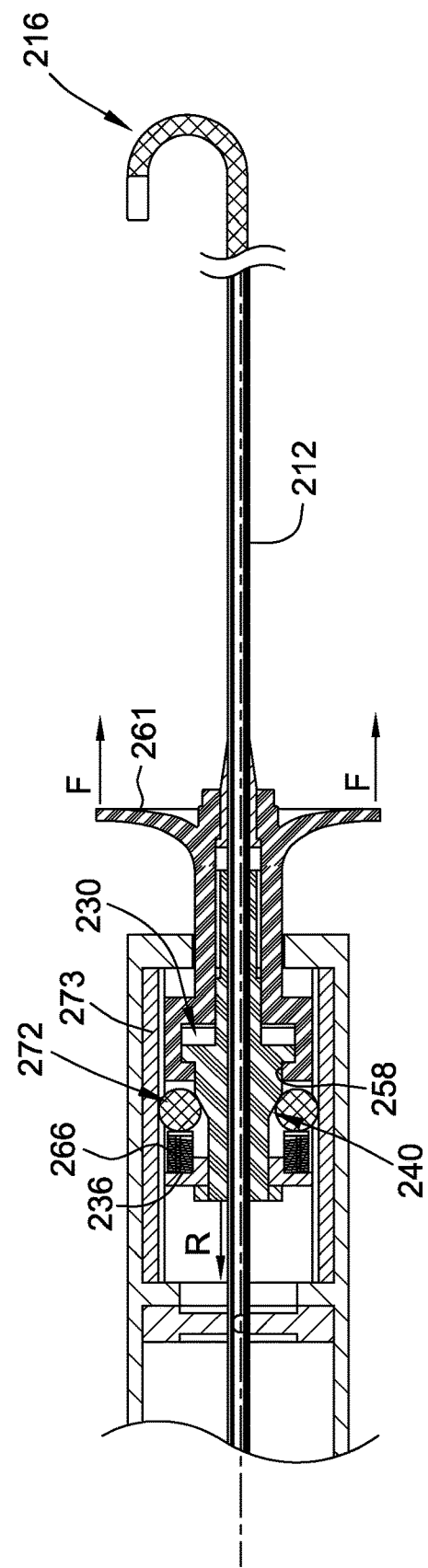

As illustrated in FIGS. 18A-18D, in use, the embodiments illustrated in FIGS. 13(A-B) and 14-17 operate similarly to the embodiment illustrated in FIG. 3. That is, distal region 216 of catheter shaft 212 is deflected from a neutral position (FIG. 18A) by distally advancing drive lever 261 with driving force F so as to cause a pull wire force R acting in the opposite direction as driving force F (FIG. 18B). As illustrated in FIG. 18B, during deflecting of distal region 216, roller springs 266 tend to be compressed, and outer restraining assembly 272 tends to move to a wider space as defined by roller rails 273 and inner restraining assembly 240 (see FIG. 13(A-B)) due to the frictional forces on outer restraining assembly 272 imposed by roller rails 273.

As illustrated in FIG. 18C, once a targeted deflected configuration is obtained, driving force F is released. When driving force F is released after the target deflection is obtained, shaft shuttle assembly 230 tends to retract proximally under the tension force R of pull wire 226, while the frictional forces of outer restraining assembly 272 imposed by roller rails 273 tend to release the compression forces of roller springs 266 between roller rails 273 and outer restraining assembly 272 such that outer restraining assembly 272 is "squeezed" into narrower spaces defined by roller rails 273 and inner restraining assembly 240 thereby introducing increased normal forces and frictional forces on outer restraining assembly 272 against the impending axial motion with respect to roller rail 273 and causing restraining assembly 228 to "self-lock" with respect to roller rails 273 affixed to actuator housing 235. The "self-locked" or "locked" configuration is illustrated in FIG. 18C.

To intentionally retract from one deflected configuration to a less deflected configuration or to the neutral state, an additional actuation force F* is imposed on drive lever 261, as illustrated in FIG. 18D, until rim 258 is in contact with outer restraining assembly 272, which has an impending proximal axial motion. Actuation force F* tends to compress roller springs 266 and allows outer restraining assembly 272 to move into wider spaces as defined by roller rails 273 and inner restraining assembly 240. This will release outer restraining assembly 272 and cause restraining assembly 228 to return to an "unlocked" or neutral state (such as the configuration illustrated in FIG. 18A).

As long as actuation force F* is equal to or greater than the overall resistance of restraining assembly 228, the retraction of shaft shuttle assembly 230 may be automatically assisted by pull wire force of retraction R. If, during retracting, actuation force F* is reduced, the retracting may discontinue and restraining assembly 228 may move to a "self-locking" position under pull wire force of retraction R at a different catheter shaft 212 configuration with less deflection present. One skilled in the art will appreciate that to move from a first deflected configuration to a second deflected configuration, wherein the second configuration is more deflected than the first configuration, no "unlocking" of restraining assembly 228 is necessary. That is, to move to the second deflected configuration with a greater extent of deflection than the first deflected configuration, driving force F is again imposed distally on drive lever 261 resulting in additional deflection of distal region 216 of catheter shaft 212. When a targeted configuration is obtained, driving force F is released and restraining assembly 228 once again assumes a new "self-locking" configuration or state. Hence, deflected and "self-locked" states of restraining assembly 228 may be spontaneous and/or reversible.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A restraining assembly for a medical device comprising:
    an inner restraining assembly positioned within an actuator housing, the inner restraining assembly comprising a proximal end surface having a first diameter and a distal end surface having a second diameter, wherein the first diameter is smaller than the second diameter, the inner restraining assembly comprising a curved outer surface extending from the proximal end surface to the distal end surface; and
    an outer restraining assembly positioned at least partially between the actuator housing and the inner restraining assembly, the outer restraining assembly having a substantially circular cross section and comprising at least one spherical shaped outer restraining member; and
    wherein the distal end surface of the inner restraining assembly extends distally past a distal end of the outer restraining assembly, and wherein at least a portion of a surface of the outer restraining assembly is configured to engage an inner surface of the actuator housing and at least a portion of a surface of the inner restraining assembly thereby providing resistance to movement of the inner restraining assembly in a proximal direction with respect to the actuator housing.

2. The restraining assembly of claim 1 wherein the at least one spherical shaped outer restraining member comprises at least two spherical shaped outer restraining members.

3. The restraining assembly of claim 2 wherein the at least two spherical shaped outer restraining members are configured to be positioned within an outer restraining assembly housing configured to circumferentially separate the at least two spherical shaped outer restraining members from one another.

4. The restraining assembly of claim 3 further comprising roller springs positioned between a flat plate and a proximal end surface of the outer restraining assembly.

5. A medical device comprising:
    a catheter shaft having a proximal region and a deflectable distal region;
    an active drive assembly comprising a drive lever, wherein the drive lever is configured to engage the proximal region of the catheter shaft and is at least partially movable with respect to an actuator housing along a longitudinal axis thereof; and
    a restraining assembly comprising:
        an inner restraining assembly positioned about the proximal region of the catheter shaft and configured to be axially movable with respect to the actuator housing via the drive lever, the inner restraining assembly comprising a proximal end surface having a first diameter and a distal end surface having a second diameter, wherein the first diameter is smaller than the second diameter, the inner restraining assembly comprising a curved outer surface extending from the proximal end surface to the distal end surface; and
        an outer restraining assembly positioned at least partially radially between the inner restraining assembly and the actuator housing, the outer restraining assembly having a substantially circular cross section and comprising at least one spherical shaped outer restraining member, wherein the distal end surface of the inner restraining assembly extends distally past a distal end of the outer restraining assembly, and wherein the restraining assembly is configured to assist in restraining the deflectable distal region of the catheter shaft in a deflected configuration.

6. The medical device of claim 5 wherein the at least one spherical shaped outer restraining member comprises at least two spherical shaped outer restraining members.

7. The medical device of claim 6 wherein the at least two spherical shaped outer restraining members are configured to be positioned within an outer restraining assembly housing configured to circumferentially separate the at least two spherical shaped outer restraining members from one another.

8. The medical device of claim 7 further comprising roller springs positioned between a flat plate and a proximal end surface of the outer restraining assembly.

9. A method of deflecting a distal region of a medical device, the method comprising:
  providing a medical device comprising:
    a catheter shaft having a proximal region and a deflectable distal region;
    an active drive assembly comprising a drive lever, wherein the drive lever is configured to engage the proximal region of the catheter shaft and is at least partially movable with respect to an actuator housing along a longitudinal axis thereof;
    a restraining assembly comprising:
      an inner restraining assembly positioned about the proximal region of the catheter shaft and configured to be axially movable with respect to the actuator housing via the drive lever, the inner restraining assembly comprising a proximal end surface having a first diameter and a distal end surface having a second diameter, wherein the first diameter is smaller than the second diameter, the inner restraining assembly comprising a curved outer surface extending from the proximal end surface to the distal end surface; and
      an outer restraining assembly positioned at least partially radially between the inner restraining assembly and the actuator housing, the outer restraining assembly having a substantially circular cross section and comprising at least one spherical shaped outer restraining member, and wherein the distal end surface of the inner restraining assembly extends distally past a distal end of the outer restraining assembly;
  distally advancing the drive lever and the inner restraining assembly with respect to the actuator housing to a position wherein the deflectable distal region of the catheter shaft is in a deflected configuration; and
  allowing the drive lever and the inner restraining assembly to at least partially retract in a proximal direction with respect to the actuator housing such that at least a portion of an outer surface of the inner restraining assembly engages at least a portion of a surface of the outer restraining assembly to create a frictional resistance therebetween sufficient to limit further proximal movement of the drive lever and the inner restraining assembly with respect to the actuator housing.

* * * * *